(12) United States Patent
Holerca et al.

(10) Patent No.: US 7,105,691 B2
(45) Date of Patent: Sep. 12, 2006

(54) ALUMINUM / ZIRCONIUM / GLYCINE ANTIPERSPIRANT ACTIVES STABILIZED WITH BETAINE

(75) Inventors: Marian Holerca, Somerset, NJ (US); Heng Cai, Yardley, PA (US)

(73) Assignee: Colgate-Palmolive Company, New York, NY (US)

( * ) Notice: Subject to any disclaimer, the term of this patent is extended or adjusted under 35 U.S.C. 154(b) by 511 days.

(21) Appl. No.: 10/607,099

(22) Filed: Jun. 26, 2003

(65) Prior Publication Data
US 2004/0265255 A1   Dec. 30, 2004

(51) Int. Cl.
C07F 19/00   (2006.01)
A61K 7/34    (2006.01)
A61K 7/38    (2006.01)

(52) U.S. Cl. ............................ 556/27; 424/66; 424/68; 424/401

(58) Field of Classification Search .................. 556/27, 556/56, 183; 424/66, 68, 401, 65
See application file for complete search history.

(56) References Cited

U.S. PATENT DOCUMENTS

| | | | |
|---|---|---|---|
| 4,075,350 A | | 2/1978 | Michaels ..................... 424/316 |
| 4,148,812 A | * | 4/1979 | Rubino et al. ................ 556/55 |
| 5,098,698 A | * | 3/1992 | Kawam et al. ............... 424/68 |
| 5,463,098 A | * | 10/1995 | Giovanniello et al. ........ 556/27 |
| 5,877,143 A | | 3/1999 | Abbas et al. ................ 510/433 |
| 6,066,314 A | | 5/2000 | Tang et al. ................... 424/65 |
| 6,451,296 B1 | * | 9/2002 | Li et al. ........................ 424/66 |
| 6,534,045 B1 | | 3/2003 | Mattai et al. |
| 6,969,510 B1 | * | 11/2005 | Holerca et al. ............... 424/65 |
| 2004/0109833 A1 | * | 6/2004 | Tang et al. ................... 424/68 |
| 2004/0258722 A1 | * | 12/2004 | Kropke et al. .............. 424/401 |
| 2005/0191256 A1 | * | 9/2005 | Holerca et al. ............... 424/66 |

FOREIGN PATENT DOCUMENTS

| | | |
|---|---|---|
| CH | 687126 | 11/1993 |
| DE | 2610225 | 3/1975 |
| DE | 2747355 | 4/1979 |
| DE | 19725087 | 12/1998 |
| EP | 0255807 | 2/1988 |
| EP | 0319486 | 6/1989 |
| EP | 0512770 | 11/1992 |
| EP | 0800819 | 4/1996 |
| EP | 1005852 | 12/1998 |
| EP | 1005853 | 11/1999 |
| FR | 2303536 | 3/1975 |
| GB | 1 479 132 | * 7/1977 |
| GB | 2354771 | 10/1999 |
| JP | 09310021 | 5/1999 |
| JP | 11345704 | 6/2001 |
| WO | WO 9118588 | 12/1991 |
| WO | WO 9219221 | 11/1992 |
| WO | WO 9723594 | 7/1997 |
| WO | WO 9746246 | 12/1997 |
| WO | WO 9813021 | 4/1998 |
| WO | WO 9951192 | 10/1999 |
| WO | WO 0067726 | 11/2000 |
| WO | WO 0139730 | 12/2000 |
| WO | WO 0147479 | 12/2000 |
| WO | WO 0162222 | 2/2001 |
| WO | WO 0178673 | 4/2001 |

OTHER PUBLICATIONS

U.S. Appl. No. 09/273,152, filed Mar. 19, 1999, Potechin et al.
U.S. Appl. No. 10/406,856, filed Apr. 4, 2003, Holerca et al.
Life Sciences, Pergamon Press, vol. 32, pp. 771-774, 1983.
Cosmetics & Toiletries—Technology Report: Antimicrobial Compositions for Controlling Body Odor by Dolores Kenney, vol. 94, pp. 13-14, Aug. 1979.
Annual Reviews: Homocysteine Metabolism by J. Selhub, pp. 217-247, 1999.
Soderling, E., Le Bell A, Kirstila V, Tenovuo, J. Betaine-containing toothpaste relives subjective symptoms of Dry mouth. Acta Odontol Scand. 1998; 56:65-69. Oslo.
Current Science, vol. 75, No. 11, Dec. 10, 1998, pp. 1153-1156, Betaine reverses toxic effects of aluminum: Implications in Alzheimer's disease and Ad-like pathology by T. Ramakrishna, S. Vatsala, V. Shobi, E. Sreekumaran, T. R. Madhav, J. Ramesh and K.R.K. Easwaran.
Barak, Anthony J., Beckenhauer, Harriet C., and Tuma, Dean J., Betaine, Ethanol, and the Liver: A Review, Apr. 21, 1995, pp. 395-398. 1996.

* cited by examiner

*Primary Examiner*—Porfirio Nazario-Gonzalez
(74) *Attorney, Agent, or Firm*—Michael F. Morgan

(57) ABSTRACT

A stabilized aluminum/zirconium/glycine salt comprising a Betaine of Formula I as additive:

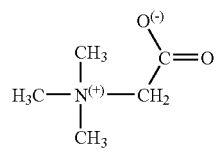

Formula I in a sufficient amount to have (a) an overall (Betaine+glycine)/Zr ratio in the range of 0.1–3.0:1, (b) a ratio of Betaine to glycine of at least 0.001:1; and (c) sufficient Betaine so that at least 0.1% of the ratio of Betaine+glycine is contributed by Betaine.

9 Claims, No Drawings

ALUMINUM / ZIRCONIUM / GLYCINE ANTIPERSPIRANT ACTIVES STABILIZED WITH BETAINE

FIELD OF THE INVENTION

This invention relates to new stabilized antiperspirant salts and a method for forming them. The use of Betaine as an additive to aluminum/zirconium/glycine salts prevents the deactivation via polymerization, which would have a negative impact on the efficacy of these salts.

BACKGROUND OF THE INVENTION

A variety of uses of betaines with long chains can be found in the surfactant art. The Betaine of this invention, however, is not a surfactant and has been found to have properties important to the field of antiperspirant salts that contain aluminum and zirconium.

The term "betaine" is used in a variety of ways. In particular, a variety of uses of betaines with long chains can be found in the surfactant art. Such betaines may be represented by the following Formula A where n>0:

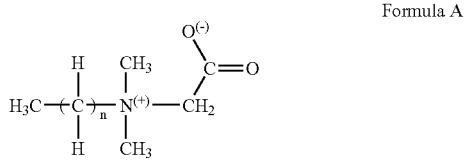

Formula A

The methyl groups can be replaced with other longer chain alkyls and can be straight chain or branched.

The Betaine (defined below) used in this invention is a natural product found in a number of plants in the Chenopodiaceae family, and also in fish and selected legumes. Extracted most often from sugar beets (*Beta Vulgaris*), it is reported as an extremely versatile molecule with a wide range of applications: food supplement, anti-irritant, skin moisturizer, skin-softening agent, skin-conditioning agent, promoter of wound healing and component in cosmetic compositions for skin aging and stressed skin.

The invention comprises a stabilized antiperspirant salt which is an aluminum/zirconium/glycine salt in combination with Betaine of Formula I:

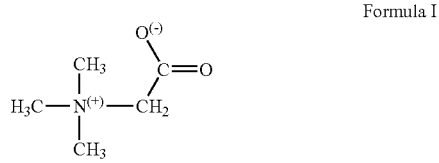

Formula I

Betaine in IUPAC nomenclature is 1-carboxy-N,N,N-trimethylmethanaminium hydroxide-inner salt, with alternative names including carboxymethyl-trimethylammonium betaine or (carboxymethyl)trimethylammonium hydroxide-inner salt or glycine betaine or glycoll betaine or glycyl betaine or trimethyl glycine or trimethylglycoll. For convenience here the material of Formula I will be referred to as Betaine.

Betaine appears in numerous patents, with a wide range of applications.

PCT Publication WO 00/67726 describes host-guest processes and formulations for delivering bio-affecting compounds. The invention relates to processes of making a composition having a host compound capable of accepting one or more bio-affecting guest compounds, and topical compositions for cosmetic or pharmaceutical uses formed by the processes. The processes comprise mixing, in any order: (i) a nonionic surfactant; (ii) an amphoteric surfactant; (iii) a solvent for the amphoteric surfactant; (iv) an aromatic compound; (v) an aluminum cation; (vi) a Lewis acid that is not a Bronsted-Lowry acid; and (vii) a Bronsted-Lowry acid.

U.S. Pat. No. 5,877,143 describes a composition containing a lamellar liquid crystalline phase which comprises betaines and amine oxides. This is a pumpable, fluid composition of amine oxide, betaine and/or sultaine is prepared with active concentration of about 36–45% of these materials by the addition of alkaline earth or aluminum salts.

German Patent DE 19725087 is related to cosmetic and dermatologic oil-in-water emulsion formulations for light protection containing hydrophobic inorganic micropigments and hydrophilic surfactants. Formulations containing suspended hydrophobic inorganic pigment microparticles in the oil phase as photoprotectants are stabilized against phase separation, migration of pigment particles into the aqueous phase, and agglomeration of the pigment particles by inclusion of a hydrophilic surfactant such as an alkyl glucoside, acyl lactylate, betaine, or coco amphoacetate, preferably together with a co-emulsifier and a water-sol. or oil-sol. UV-B filtering agent.

PCT Publication WO 97/23594 describes skin cleanser compositions with enhanced antimicrobial activity. The title compounds, useful for cleansing the skin and deposition of an antimicrobial agent onto the skin, comprise 0.1–30% of an amphoteric, zwitterionic, nonionic, anionic and/or cationic emulsifier, 0.00001–5% of an Ag compound deposited on a particulate inert support material as antimicrobial agent, and $H_2O$. Cetyl betaine is used.

Swiss Patent CH 687126 relates to cosmetic compositions containing vegetable extract and trace elements complexes. Described are cosmetic compositions containing vegetable extract and trace elements complexes based on calcium and magnesium. Cocamidopropyl betaine is used.

Japanese Patent JP 52093633 describes chemical polishing solutions for aluminum and its alloys. Myristylbetaine is used.

British Patent GB 2354771 relates to bactericide combinations in detergents. The detergent comprises a bactericide in combination with an anionic, cationic, nonionic or amphoteric surfactant which has a C12–18 alkyl group as the longest chain attached to the hydrophilic moiety.

Japanese Patent JP 2001163752 describes cosmetics containing glossy polymer powders and antiperspirants. This invention relates to long-lasting cosmetic makeup compositions comprising plate-type glossy polymer powders and antiperspirants.

European Patent EP 1005853 describes the use of betaines as antiperspirants. Mono-, di-, and trimethylammonio-substituted carboxylic acids $R^1R^2R^3N+(CH_2)nC(O)O-$ ($R^1-R^3=H$, Me; n=1–10) are active as antiperspirants and are compatible with the skin and with other conventional constituents of antiperspirant and deodorant compositions.

European Patent EP 1005852 describes the use of functionally substituted betaines as antiperspirants. Mono-, di-, and trimethylammonio-substituted carboxylic acids $R^1R^2R^3N^+(CH_2)nCHX(CH_2)mC(O)O-$ and/or $X(CH_2)nCH(N^+R1R2R3)(CH2)mC(O)O-$ (R1–R3=H, Me; m, n=1–8) are active as antiperspirants and are compatible with the skin and with other conventional constituents of antiperspirant and deodorant compositions.

Japanese Patent JP 11130652 discloses skin-conditioning and -moisturizing cosmetics containing clay minerals and low-molecular-weight betaines.

German Patent DE 2610225 describes aluminum salts of Betaine chloride being useful as ulcer inhibitors, for treatment of gastritis, to promote wound healing, and as antiperspirants and deodorants.

PCT Publication WO 01/62222 describes cosmetic compositions containing phospholipids and quaternary amines. The invention relates to a cosmetic composition, especially for use on aging and/or stressed skin, the composition comprising, in addition to water, at least one substance that forms lamellar structures with water. The composition further comprises (a) at least one compound that contains a functional group —CH$_2$—N+—(CH$_3$)$_3$; (b) and/or at least one metabolite of the compound;.

PCT Publication WO 01/47479, owned by the same owner as the present case, describes cosmetic moisturizing compositions containing quaternary ammonium compounds. A composition useful for moisturizing skin which comprises (a) a moisturizer such as Me$_3$N$^+$X$^{-1}$ (X=CH$_2$OH or, CHOHCH$_2$CO$_2$—, or mixtures and when X does not bear a negative charge, the compound is a salt) and a skin compatible carrier.

PCT Publication WO 01/39730 describes a cosmetic composition containing peat and Betaine suitable for cosmetic masks for the face, chin and/or scalp.

PCT Publication WO 97/46246 is related to complex preparations containing Betaine. Preparations, especially for topical use in these preparations, penetrates deep into the tissues where it stimulates cellular and physiological processes.

PCT Publication WO 91/18588 presents a method of reducing the irritating properties of a cosmetic composition by addition of Betaine derivatives.

Japanese Patent JP 03033266 describes modified fabrics for controlling pH change in skin during sweating such as those treated with a mixture including dodecyl betaine (I) 10.

Thus, Betaine is described as an antiperspirant, deodorant, anti-irritant, skin moisturizer, skin-softening agent, skin-conditioning agent, promoter of wound healing, component in cosmetic compositions for skin aging and stressed skin, anti-inflammatory and tissue regenerating agent in topical skin care compositions, pH control agent on fabrics during sweating, component in detergent compositions with bactericide action, component in collagen type I activating complex in skin, surfactant in sunscreen compositions, complexing agent in aluminum liquid crystalline phases, and complexing agent for aluminum in chemical polishing solutions.

BRIEF SUMMARY OF THE INVENTION

This invention comprises aluminum/zirconium salts containing a complexation agent such as glycine and further stabilized with Betaine as complexation agent and buffer agent. The amount of Betaine that is used should be sufficient to have an overall Betaine+glycine to Zr ratio in the range of 0.1–3.0:1, and preferably in the range of 0.7–1.5:1, with a ratio of Betaine to glycine of at least 0.001:1.

DETAILED DESCRIPTION OF THE INVENTION

The invention comprises a stabilized aluminum/zirconium/glycine salt comprising a Betaine of Formula I:

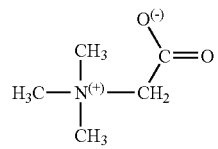

Formula I in a sufficient amount (a) to have an overall (Betaine+glycine)/Zr ratio in the range of 0.1–3.0:1, (b) a ratio of Betaine to glycine of at least 0.001:1; and (c) sufficient Betaine so that at least 0.1% of the ratio of Betaine+glycine is contributed by Betaine.

The improved salts of this invention may be based on any aluminum/zirconium/glycine antiperspirant salt used as an antiperspirant. Such salts should include glycine, and the present invention uses Betaine as an additional additive. The total amount of glycine and Betaine in the salt should be such that the ratio described above is maintained, but provided that at least 0.1% of the ratio is contributed by Betaine. It should be noted that the present invention uses Betaine as a complexation agent to supplement the action of glycine, and it is shown here that addition of Betaine has a better effect than that of additional increase in glycine. The use of Betaine in a glycine-free environment is covered in a copending case. (Attorney Docket # IR 7073, filed May 30, 2003).

Suitable salts that may be used with this invention include conventional aluminum/zirconium/glycine salts, as well as aluminum/zirconium salts complexed with a complexing agent, such as glycols, as are known in the art in form of aluminum zirconium chlorohydrex propylene glycol complex, aluminum zirconium chlorohydrex tripropylene glycol complex, aluminum zirconium chlorohydrex dipropylene glycol complex and mixtures of any of the foregoing.

See each of European Patent Application Number. 512,770 A1 and PCT case WO 92/19221, the contents of each of which are incorporated herein by reference in their entirety, for disclosures of antiperspirant active materials. Suitable materials include (but are not limited to) zirconyl hydroxychlorides, zirconyl oxychlorides, basic aluminum chlorides combined with zirconyl oxychlorides and hydroxychlorides, and organic complexes of each of basic aluminum chlorides with zirconyl oxychlorides and hydroxychlorides and mixtures of any of the foregoing. These include, by way of example (and not of a limiting nature) zirconyl hydroxychloride, aluminum-zirconium glycine complex (for example, aluminum zirconium trichlorohydrex gly, aluminum zirconium pentachlorohydrex gly, aluminum zirconium tetrachlorohydrex gly and aluminum zirconium octachlorohydrex gly), aluminum zirconium trichlorohydrex gly propylene glycol complex, aluminum zirconium trichlorohydrex gly dipropylene glycol complex, aluminum zirconium tetrachlorohydrex gly propylene glycol complex, aluminum zirconium tetrachlorohydrex gly dipropylene glycol complex, and mixtures of any of the foregoing. Generally, the foregoing metal antiperspirant active materials are antiperspirant active metal salts.

Preferred antiperspirant actives that can be incorporated in the formulated compositions of the present invention include the stabilized aluminum/zirconium salts, especially those having enhanced efficacy due to improved molecular distribution, known in the art and discussed, for example, in PCT No. WO92/19221, the contents of which are incorporated by reference in their entirety herein. Particular actives include Westchlor A2Z 4105 aluminum zirconium tetrachlorohydrex gly propylene glycol complex, (from Westwood Chemical Corporation, Middletown, N.Y.); Westchlor ZR 35B aluminum zirconium tetrachlorhydrex gly, and Rezal 36 GP and AZP 908 aluminum zirconium tetrachlorhydrex glycine both from Reheis, Berkeley Heights, N.J. as well as Rezal AZZ 902 aluminum zirconium trichlorhydrex glycine from Reheis. Also, Summit actives Z522, Z551 and Z576 (from Summit Research Labs, Huguenot, N.Y.) can be used. In general, the metal:chloride mole ratio is in the range of 2.1–0.9:1 for such salts.

Actives of special interest because they form low RI solutions include: Westchlor Zr 35BX3 (30–35% actives in water) from Westwood Chemical Company; Rezal 36G (46% in water) from Reheis Inc.; Summit AZG-368 (28–32% in water) from Summit Research Labs; and Reach 301 (39% in water) from Reheis Inc. In general, the metal:chloride mole ratio is approximately 1.4:1 for such salts.

In one particular type of salt of interest, an aluminum zirconium tetra salt with glycine is used wherein aluminum zirconium tetrachlorohydrex glycine salt having a metal to chloride ratio in the range of 0.9–1.2:1 (especially in the range of 0.9–1.1:1 and, more particularly in the range of 0.9–1.0:1); and a glycine:zirconium mole ratio greater than 1.3:1, particularly greater than 1.4:1.

Antiperspirant actives can be incorporated into formulated compositions according to the present invention in amounts in the range of 5–25% (on an anhydrous solids basis), preferably 7–20%, by weight, of the total weight of the composition. The amount used will depend on the formulation of the composition. At amounts at the higher end of the range (especially in a range of 9–20% or 9–25%, a good antiperspirant effect can be expected. As noted above, the active and Betaine are preferably included in the compositions of the invention by premixing the active and Betaine with water and possibly a small amount of propylene glycol.

The main advantage of the stabilized salts of the present invention is that they have improved stability over salts that contain only glycine or glycols or no stabilizing agent at all.

The polymerization of the antiperspirant actives in aqueous solutions and the correspondent gelation process were followed by monitoring the molecular weight profile of the polyoxohalides in time by size exclusion chromatography (SEC). Size exclusion chromatography ("SEC") or gel permeation chromatography ("GPC") are methods frequently used for obtaining information on polymer distribution in antiperspirant salt solutions. With appropriate chromatographic columns, at least five distinctive groups of polymer species can be detected in a zirconium/aluminum/glycine complex (ZAG), appearing in a chromatogram as peaks 1, 2, 3, 4 and a peak known as "5,6". Peak 1 is the larger Zr species (greater than 60 Angstroms). Peaks 2 and 3 are larger aluminum species. Peak 4 is smaller aluminum species (aluminum oligomers) and has been correlated with enhanced efficacy for both ACH and ZAG salts. Peak 5,6 is the smallest aluminum species. The relative retention time ("Kd") for each of these peaks varies depending on the experimental conditions. This technique is also applicable to the salts of this invention which also contain Betaine. Data for Tables was obtained using the SEC method described in an issued patent owned by the same company as this case, U.S. Pat. No. 6,066,314, incorporate by reference as to the test method described therein.

The design of modern AP salts aims at actives with high levels of low molecular weight Al and Zr species, which is reflected in a SEC trace that has intense Peaks 4 and 5 and a low Peak 1. Throughout the present study, the levels of the species corresponding to these three peaks are estimated based on the following ratios:

$$f_{Pi} = \frac{Pi}{\Sigma Pj} \quad i = 1, 2, 3, 4, 5; \quad j = 2, 3, 4, 5$$

where $f_{Pi}$ is the fraction of peak i, and Pi or Pj are the intensity of peaks Pi or Pj, respectively. We will correlate the amount of high molecular weight Zr with the fraction of Peak 1, i.e. $f_{P1}$, and we will correlate the amount of low molecular weight Al species with the fraction of Peaks 4 and 5, i.e. $f_{P4}$ and $f_{P5}$. In brief, an ideal antiperspirant salt would have a very low $f_{P1}$, a high $f_{P4}$ and a high $f_{P5}$ and their correspondent rate of change would be minimal.

Using the technique described above, the polymerization of various antiperspirant actives in aqueous solutions and the correspondent gelation process over time was followed by monitoring the molecular weight by size exclusion chromatography (SEC) in the presence of Betaine. It was determined that (1) addition of 1–15% Betaine to 30% solutions of Reheis AZP 908, AZZ 902, or Summit Z551 leads to the stabilization of these actives; (2) the stabilizing effect increases with the concentration of Betaine, with an optimum amount of Betaine being about 8% by weight; (3) the stabilizing effect is enhanced at higher temperatures, 40 degrees C. (104 degrees F.); (4) the stabilizing effect of Betaine is slightly superior to that of glycine; (5) the gelation process is retarded or stopped for up to 1 year.

The enhanced salts of this invention may be used to formulate antiperspirants having improved efficacy. Such antiperspirants include solids such as sticks and creams (creams sometimes being included in the term "soft solid"), gels, liquids (such as are suitable for roll-on products), and aerosols. The forms of these products may be suspensions or emulsions.

Examples of suitable formulations include the following:

Sticks—Stick products may be made with conventional gelling agents such as stearyl alcohol and dibenzylidene sorbitol. A sample formulation is as follows:

40–55% (particularly 45%) cyclomethicone (especially D5 cyclomethicone)

20–30% (particularly 21%) stearyl alcohol

7–15% (particularly 10%) talc

15–22% (particularly 22%) antiperspirant active in powder form

1–3% (particularly 2%) fragrance

Roll Ons

45–65% (particularly 55%) cyclomethicone (especially D5 cyclomethicone)

0.1–10% (particularly 3%) cyclomethicone/dimethicone copolyol (such as Dow Corning 2-5185 C)

10–25% (particularly 20%) antiperspirant active in solution form (25–45% actives on an anhydrous basis in water)

5–30% (particularly 20%) water

1–3% (particularly 2%) fragrance

Soft solids—Soft solids may be made with formulations described in co-pending patent application (U.S. Ser. No. 9/273,152 and PCT Publication WO 99/51192). A sample formulation is as follows:

- 40–70% (particularly 50%) elastomer in cyclomethicone (KSG-15 from Shin-Etsu)
- 5–15% (particularly 6%) polyethylene (for example, beads having a density in the range of 0.91–0.98 g/cm$^3$ and an average particle size in the range of 5–40 microns)
- 10–20% (particularly 15%) C12–15 alkylbenzoate (FINSOLV TN from Finetex)
- 0.1–25% (particularly 22%) antiperspirant active in powder form
- 1–15% (particularly 5%) dimethicone (particularly with a viscosity of 100 centistokes)
- 1–3% (particularly 2%) fragrance Gels—Gels may be made with a variety of formulations such as

- 5–50% (particularly 29%) cyclomethicone (particularly D5)
- 0.1–10% (particularly 3%) cyclomethicone/dimethicone copolyol (such as Dow Corning 2-5185 C)
- 0–10% (particularly 5%) hydrogenated polyisobutene 250
- 0–10% (particularly 5%) C12–15 alkylbenzoate (FINSOLV TN from Finetex)
- 0–10% (particularly 5%) dimethicone (particularly with a viscosity of 100 centistokes)
- 0.1–25% (particularly 20%) antiperspirant active in powder form or 10–25% (particularly 20%) of active in solution (25–45% actives on an anhydrous basis)
- 5–50% (particularly 30%) water
- 1–3% (particularly 2%) fragrance Note that in the explanation of the invention, where water is listed it is intended to count the contribution of the water present in the antiperspirant solution as part of the overall water content. Thus, water is sometimes listed as part of the actives solution or sometimes listed separately.

In a preferred embodiment the refractive indices of the external and internal phases are matched within 0.005 to obtain a clear product.

Particular formulations of interest include:

Formulation A:
- 0.5–2.5% dimethicone copolyol (for example, Dow Corning 2-5185C (48%))
- 55–65% elastomer in cyclomethicone (for example, DC-9040 from Dow Corning Corporation (Midland, Mich.) or KSG-15 from Shin-Etsu Silicones of America (Akron, Ohio))
- 1–10% PPG-3 myristyl ether
- 10–25% antiperspirant active of the invention
- 10–25% water
- 0.5–1.5% fragrance Formulation B
- 1.0–3.0% dimethicone copolyol (for example, Dow Corning 2-5185C (48%))
- 40–60% elastomer in cyclomethicone (for example, DC-9040 from Dow Corning Corporation (Midland, Mich.) or KSG-15 from Shin-Etsu Silicones of America (Akron, Ohio))
- 1–5% cyclomethicone (in addition to that found in the elastomer)
- 4–12% PPG-3 myristyl ether
- 15–30% antiperspirant active of the invention
- 15–35% water
- 0.5–1.5% fragrance Formulation C
- 1.0–3.0% dimethicone copolyol (for example, Dow Corning 2-5185C (48%))
- 1–10% hydrogenated polyisobutene (for example, Fancol™ Polyiso 250)
- 40–55% elastomer in cyclomethicone (for example, DC-9040 from Dow Corning Corporation (Midland, Mich.) or KSG-15 from Shin-Etsu Silicones of America (Akron, Ohio))
- 3–8% PPG-3 myristyl ether
- 15–20% antiperspirant active of the invention 20–30% water
- 1.0–3.0% fragrance Formulation D
- 1.0–3.0% dimethicone copolyol (for example, Dow Corning 2-5185C (48%))
- 40–60% elastomer in cyclomethicone (for example, DC-9040 from Dow Corning Corporation (Midland, Mich.) or KSG-15 from Shin-Etsu Silicones of America (Akron, Ohio))
- 3–8% PPG-3 myristyl ether
- 15–30% antiperspirant active of the invention
- 15–30% water
- 0.5–1.5% fragrance
- 1–10% diethylhexyl naphthalate Formulation E
- 0.5–2.5% dimethicone copolyol (for example, Dow Corning 2-5185C (48%))
- 60–70% elastomer in cyclomethicone (for example, DC-9040 from Dow Corning Corporation (Midland, Mich.) or KSG-15 from Shin-Etsu Silicones of America (Akron, Ohio))
- 7–10% antiperspirant active of the invention
- 25–35% water
- 1–10% methylpropylene diol (MPDiol)
- 0.5–1.5% fragrance Formulation F
- 1.0–3.0% dimethicone copolyol (for example, Dow Corning 2-5185C (48%))
- 6–10% hydrogenated polyisobutene (for example, Fancol™ Polyiso 250)
- 35–45% elastomer in cyclomethicone (for example, DC-9040 from Dow Corning Corporation (Midland, Mich.) or KSG-15 from Shin-Etsu Silicones of America (Akron, Ohio))
- 6–10% PPG-3 myristyl ether
- 40–50% antiperspirant active of the invention as 43% active in water no additional water
- 0.5–1.0% fragrance Formulation G
- 0.1–0.6% dimethicone copolyol (for example, Dow Corning 2-5185C (48%))
- 4–7% hydrogenated polyisobutene (for example, Fancol™ Polyiso 250)
- 40–50% elastomer in cyclomethicone (for example, DC-9040 from Dow Corning Corporation (Midland, Mich.) or KSG-15 from Shin-Etsu Silicones of America (Akron, Ohio))
- 4–7% PPG-3 myristyl ether
- 40–50% antiperspirant active of the invention as 43% active in water no additional water
- 0.5–1.0% fragrance Formulation H
- 0.5–2.0% dimethicone copolyol (for example, Dow Corning 2-5185C (48%))

1–7% hydrogenated polyisobutene (for example, Fancol™ Polyiso 250)
40–50% elastomer in cyclomethicone (for example, DC-9040 from Dow Corning Corporation (Midland, Mich.) or KSG-15 from Shin-Etsu Silicones of America (Akron, Ohio))
45–55% antiperspirant active as 43% active of the invention in water no additional water
0.5–1.5% fragrance Formulation I
2–7% dimethicone copolyol (for example, Dow Corning 2-5185C (48%))
0.1–1% Oleath-20
1–5% C12–15 alkyl benzoate (FINSOLV TN)
15–25% elastomer in cyclomethicone (for example, DC-9040 from Dow Corning Corporation (Midland, Mich.) or KSG-15 from Shin-Etsu Silicones of America (Akron, Ohio))
15–25% antiperspirant active
15–30% water
0.5–1.5% fragrance Examples of such products with the salt made in accordance with this invention include:

(a) A stick antiperspirant and/or deodorant comprising: 40–55% cyclomethicone; 20–30% stearyl alcohol; 7–15% talc; 15–22% of a salt according to Claim 1 added in powder form; and 1–3% fragrance.

(b) A roll-on antiperspirant and/or deodorant comprising: 45–65% cyclomethicone; 0.1–10% cyclomethicone/dimethicone copolyol; 10–25% of a salt according to Claim 1 in a solution as 25–45% actives on an anhydrous basis in water; 5–30% water; and 1–3% fragrance.

(c) A soft solid antiperspirant and/or deodorant comprising: 40–70% elastomer in cyclomethicone; 5–15% polyethylene beads having a density in the range of 0.91–0.98 g/cm$^3$ and an average particle size in the range of 5–40 microns; 10–20% C12–15 alkylbenzoate; 0.1–25%% of a salt according to Claim 1 added in powder form; 1–15% dimethicone; and 1–3% fragrance.

(d) A gel antiperspirant and/or deodorant comprising: 5–50% cyclomethicone; 0.1–10% cyclomethicone/dimethicone copolyol; 0–10% hydrogenated polyisobutene 250; 0–10% C12–15 alkylbenzoate; 0–10% dimethicone; 0.1–25% of a salt according to Claim 1 added in powder form or as 10–25% of active in solution (25–45% actives on an anhydrous basis); 5–50%; and 1–3% fragrance.

The cosmetic composition according to the present invention can be packaged in conventional containers, using conventional techniques. Where a gel, cream or soft-solid cosmetic composition is produced, the composition can be introduced into a dispensing package (for example, conventional packages for gels with glide on applicators, jars where the gel or cream is applied by hand, and newer style packages having a top surface with pores) as conventionally done in the art. Thereafter, the product can be dispensed from the dispensing package as conventionally done in the art, to deposit the active material, for example, on the skin. For sticks, sprays, aerosols and roll-ons the compositions can be placed in a conventional types of container (with the inclusion of propellants in aerosols). This provides good deposition of the active material on the skin.

Compositions of the present invention can be formulated as clear, translucent or opaque products, although clear products are preferred. A desired feature of the present invention is that a clear, or transparent, cosmetic composition, (for example, a clear or transparent deodorant or antiperspirant composition) can be provided. The term clear or transparent according to the present invention is intended to connote its usual dictionary definition; thus, a clear liquid or gel antiperspirant composition of the present invention allows ready viewing of objects behind it. By contrast, a translucent composition, although allowing light to pass through, causes the light to be scattered so that it will be impossible to see clearly objects behind the translucent composition. An opaque composition does not allow light to pass therethrough. Within the context of the present invention, a gel or stick is deemed to be transparent or clear if the maximum transmittance of light of any wavelength in the range 400–800 nm through a sample 1 cm thick is at least 35%, preferably at least 50%. The gel or liquid is deemed translucent if the maximum transmittance of such light through the sample is between 2% and less than 35%. A gel or liquid is deemed opaque if the maximum transmittance of light is less than 2%. The transmittance can be measured by placing a sample of the aforementioned thickness into a light beam of a spectrophotometer whose working range includes the visible spectrum, such as a Bausch & Lomb Spectronic 88 Spectrophotometer. As to this definition of clear, see European Patent Application Publication No. 291,334 A2. Thus, according to the present invention, there are differences between transparent (clear), translucent and opaque compositions.

EXAMPLES

The following Examples are offered as illustrative of the invention and are not to be construed as limitations thereon. In the Examples and elsewhere in the description of the invention, chemical symbols and terminology have their usual and customary meanings. In the Examples as elsewhere in this application values for n, m, etc. in formulas, molecular weights and degree of ethoxylation or propoxylation are averages. Temperatures are in degrees C. unless otherwise indicated. If alcohol is used, it is 95% unless otherwise indicated. Unless otherwise indicated, "water" or "D.I. water" mean deionized water. As is true throughout the application, the amounts of the components are in weight percents based on the standard described; if no other standard is described then the total weight of the composition is to be inferred. Various names of chemical components include those listed in the *CTFA International Cosmetic Ingredient Dictionary* (Cosmetics, Toiletry and Fragrance Association, Inc., 7$^{th}$ ed. 1997).

EXAMPLES

Examples of antiperspirant actives used for our experiments are Reheis Reach AZP-908, AZZ-902, and Summit Z-522 with specifications described in Tables. Summit Z-522 was the only active received as a 29% solution, and aged during transport and storage for approximately 4 weeks prior to being used in the experiments. All other active solutions were freshly produced in our laboratory from their corresponding powder form by dissolution in water. Typically, the tested active solution was prepared by dissolving the antiperspirant active powder in deionized ("DI") water at room temperature, with stirring to form a 29–30% solution. This was followed by the addition of powdered Betaine or glycine in the desired concentration, and stirring at room temperature until clear. Subsequently, the solution was stored as multiple 10 ml sealed samples in disposable scintillation vials. The SEC analysis used 2 ml of such solution, which was diluted with 4 ml DI water immediately prior to analysis. The solutions were followed at room temperature and at 40 degrees C. (104 degrees F.), over a period of 12 months or until sampling was no longer possible due to the formation of a hard gel. The samples were diluted to 10% solution by adding distilled water and shaking, and 2 microliters of the solution were then injected into the SEC instrument for analysis. Note that the DYB color standard is a well accepted standard used in the personal care industry.

TABLE A

Specifications and Analysis Data for Reheis Reach AZP 908

| Parameter | Specification | Analysis |
|---|---|---|
| Color: DYB | 4.0 Max. | 2.1 |
| Aluminum | 14.5–15.5% | 14.9% |
| Zirconium | 13.0–15.5% | 14.1% |
| Chloride | 17.0–18.5% | 17.6% |
| Glycine | 10.5–13.5% | 11.7% |
| Metals/Chloride | 0.9–1.5 | 1.4 |
| Aluminum/Zirconium | 3.4–3.8 | 3.6 |
| pH of 15% soln. | 3.7–4.1 | 3.8 |
| Particles thru 400 mesh | 100% Min | 100% |
| Particles < 10 microns | 95% Min | 96 |
| Description | White to off white powder | Pass |
| % Anhydrous Aluminum | 69.6–85.0% | 76.7% |
| Zirconium tetrachlorohydrex | 90.0–110.0% of label amount | Pass |

TABLE B

Specifications and Analysis Data for Reheis Reach AZZ 902

| Parameter | Specification | Analysis |
|---|---|---|
| Aluminum | 13.5–15.2% | 14.7% |
| Zirconium | 13.5–16.0% | 15.0% |
| Chloride | 14.0–17.5% | 15.8% |
| Glycine | 13.5–16.5% | 14.1% |
| Metals/Chloride | NA | 1.59 |
| Aluminum/Zirconium |  | 3.31 |
| pH of 25% soln. | 3.6–4.4 | 3.8 |
| Particles thru 400 mesh | 100% Min | 100% |
| Particles < 10 microns | 95% Min | 95 |
| Description | White to off white powder | Pass |

TABLE C

Analysis Data for Summit Z-522

| Parameter | Z-522 |
|---|---|
| Aluminum | 5.3% |
| Zirconium | 5.0% |
| Chloride | 8.6% |
| Glycine | 5.3% |
| Metals/Chloride | 1.04 |
| Aluminum/Zirconium | 3.64 |
| Glycine/Zirconium | 1.28 |
| pH of 15% soln. | 3.4–4.2 |
| % Anhydrous | 28% |
| Description | 29% aq. hazy soln. |

Example 1

AZP 908 with Betaine

Table D presents the results for the polymerization of AZP 908 at different Betaine concentrations, aged at room temperature. Little alteration of the Al species is noted during aging, $f_{P4} \approx 0.1$ and $f_{P5} \approx 0.2$ regardless of the concentration in Betaine. However, there is a good effect on the deactivation rate of Zr species, with a retardation of the polymerization process. The effect is directional with an increase in retardation when the concentration of Betaine is increased from 1% to 5%. In general, Betaine slows down the Zr polymerization process; and this effect is better when increasing the Zr/Betaine ratio. Note that the solutions with Betaine are still clear, low viscosity liquids even after 1 year (360 days), while the AZP 908 solution without Betaine is typically a gel after 9 months.

TABLE D

SEC results for the 30% AZP-908 solution with various concentrations of Betaine while aging at room temperature.

| Time (days) | 1% Betaine | | | 3% Betaine | | | 5% Betaine | | |
|---|---|---|---|---|---|---|---|---|---|
| | Peak 1 | Peak 4 | Peak 5 | Peak 1 | Peak 4 | Peak 5 | Peak 1 | Peak 4 | Peak 5 |
| 1 | 0.167 | 0.118 | 0.185 | 0.133 | 0.114 | 0.189 | 0.109 | 0.104 | 0.188 |
| 2 | 0.145 | 0.114 | 0.188 | 0.140 | 0.109 | 0.185 | 0.096 | 0.103 | 0.192 |
| 4 | 0.175 | 0.119 | 0.198 | 0.143 | 0.110 | 0.190 | 0.111 | 0.102 | 0.188 |
| 7 | 0.197 | 0.119 | 0.195 | 0.168 | 0.113 | 0.188 | 0.151 | 0.105 | 0.194 |
| 11 | 0.236 | 0.118 | 0.196 | 0.184 | 0.110 | 0.191 | 0.152 | 0.103 | 0.190 |
| 14 | 0.239 | 0.124 | 0.193 | 0.193 | 0.113 | 0.187 | 0.155 | 0.103 | 0.192 |
| 25 | 0.269 | 0.117 | 0.196 | 0.222 | 0.114 | 0.189 | 0.200 | 0.108 | 0.190 |
| 41 | 0.293 | 0.117 | 0.198 | 0.256 | 0.110 | 0.205 | 0.204 | 0.106 | 0.194 |
| 63 | 0.292 | 0.120 | 0.198 | 0.242 | 0.111 | 0.194 | 0.230 | 0.106 | 0.196 |
| 92 | 0.303 | 0.108 | 0.202 | 0.264 | 0.105 | 0.199 | 0.246 | 0.093 | 0.197 |
| 148 | 0.286 | 0.092 | 0.201 | 0.264 | 0.090 | 0.206 | 0.258 | 0.078 | 0.204 |
| 218 | 0.284 | 0.081 | 0.208 | 0.274 | 0.076 | 0.205 | 0.261 | 0.070 | 0.214 |
| 360 | *liq | *liq | *liq | *liq | *liq | *liq | *liq | *liq | *liq |

*liq - sample observed as a free-flowing liquid (visual observation, no SEC data run).

For AZP 908 solutions, the experiments at higher temperature show that Betaine can induce a major reduction of the amount of new high molecular weight Zr species (Table E), while the results from room temperature conditions indicate only minor retardation of polymerization. The addition of 1% Betaine has a lesser affect on polymerization of zirconium, while addition of 5% and 8% Betaine gives good stability with $f_{P1} \approx 0.25$ at 7 and 20 weeks, respectively. The sample with 1% Betaine presents gellation at 327 days, while samples with 5% and 8% Betaine are free flowing liquid solutions even at 720 days.

F. The stabilization effect is better than in the case of AZP 908 since the polymerization is not only retarded, but the equilibrium values are significantly reduced. The addition of 3% Betaine results in the stabilization of the Zr species at $f_{P1} \approx 0.22$, while an addition of 8% or more Betaine completely eliminates the polymerization of Zr, $f_{P1} \approx 0.15$. On the other hand, the Al species are less influenced by these amounts of Betaine, resulting in equilibrium values of $f_{P4} \approx 0.16$ and $f_{P5} \approx 0.12$. Since Zr is known to be more reactive that Al, it is expected that at higher concentrations of Betaine, exceeding the values of Zr saturation, a major effect on the Al species is expected. No gellation was observed for these samples at 720 days.

TABLE E

SEC results for the 30% AZP-908 solution with various concentrations of Betaine while aging at 40 degrees C.

| Time | 1% Betaine | | | 5% Betaine | | | 8% Betaine | | |
|---|---|---|---|---|---|---|---|---|---|
| (days) | Peak 1 | Peak 4 | Peak 5 | Peak 1 | Peak 4 | Peak 5 | Peak 1 | Peak 4 | Peak 5 |
| 21 | 0.367 | 0.103 | 0.216 | 0.221 | 0.104 | 0.219 | | | |
| 22 | | | | | | | 0.160 | 0.096 | 0.213 |
| 42 | 0.389 | 0.074 | 0.221 | 0.243 | 0.095 | 0.222 | 0.155 | 0.084 | 0.215 |
| 64 | | | | | | | 0.167 | 0.101 | 0.228 |
| 72 | 0.365 | 0.047 | 0.228 | 0.255 | 0.068 | 0.225 | | | |
| 78 | | | | | | | 0.208 | 0.086 | 0.218 |
| 105 | 0.408 | 0.293 | 0.244 | 0.262 | 0.241 | 0.224 | | | |
| 108 | | | | | | | 0.224 | 0.061 | 0.220 |
| 136 | *liq | *liq | *liq | | | | 0.244 | 0.050 | 0.217 |
| 327 | **gel | **gel | **gel | | | | | | |
| 720 | | | | *liq | *liq | *liq | *liq | *liq | *liq |

*liq - sample observed as a free-flowing liquid (visual observation, no SEC data run).
**gel - sample observed as a gelled mass that does not flow (visual observation).

Example 2

AZZ 902 with Betaine

The polymerization of AZZ 902 in solution at room temperature in the presence of Betaine is presented in Table

TABLE F

SEC results for the 30% AZZ-902 solution with various concentrations of Betaine while aging at room temperature.

| Time | 3% Betaine | | | 8% Betaine | | | 15% Betaine | | |
|---|---|---|---|---|---|---|---|---|---|
| (days) | Peak 1 | Peak 4 | Peak 5 | Peak 1 | Peak 4 | Peak 5 | Peak 1 | Peak 4 | Peak 5 |
| 3 | | | | | | | 0.115 | 0.263 | 0.118 |
| 4 | 0.173 | 0.352 | 0.129 | | | | | | |
| 7 | 0.178 | 0.244 | 0.125 | | | | 0.106 | 0.239 | 0.111 |
| 8 | | | | 0.150 | 0.230 | 0.109 | | | |
| 10 | | | | | | | 0.099 | 0.232 | 0.107 |
| 11 | 0.185 | 0.253 | 0.113 | 0.139 | 0.222 | 0.108 | | | |
| 14 | | | | | | | 0.115 | 0.218 | 0.118 |
| 18 | 0.211 | 0.237 | 0.113 | | | | | | |
| 21 | | | | | | | 0.111 | 0.206 | 0.118 |
| 25 | 0.193 | 0.223 | 0.126 | 0.138 | 0.203 | 0.108 | | | |
| 28 | | | | | | | 0.087 | 0.206 | 0.099 |
| 32 | 0.222 | 0.216 | 0.107 | | | | | | |
| 42 | | | | | | | 0.091 | 0.192 | 0.106 |
| 46 | 0.216 | 0.202 | 0.110 | 0.155 | 0.178 | 0.110 | | | |
| 56 | | | | | | | 0.085 | 0.184 | 0.106 |
| 70 | | | | 0.157 | 0.168 | 0.112 | | | |
| 74 | 0.216 | 0.184 | 0.121 | | | | | | |
| 84 | | | | | | | 0.079 | 0.170 | 0.110 |
| 101 | | | | | | | 0.084 | 0.159 | 0.110 |
| 109 | 0.227 | 0.165 | 0.134 | | | | | | |
| 132 | | | | 0.153 | 0.139 | 0.118 | | | |

TABLE F-continued

SEC results for the 30% AZZ-902 solution with various concentrations of Betaine while aging at room temperature.

| Time | 3% Betaine | | | 8% Betaine | | | 15% Betaine | | |
|---|---|---|---|---|---|---|---|---|---|
| (days) | Peak 1 | Peak 4 | Peak 5 | Peak 1 | Peak 4 | Peak 5 | Peak 1 | Peak 4 | Peak 5 |
| 144 | 0.218 | 0.144 | 0.130 | | | | 0.090 | 0.153 | 0.108 |
| 720 | *liq | *liq | *liq | *liq | *liq | *liq | *liq | *liq | *liq |

*liq - sample observed as a free-flowing liquid (visual observation, no SEC data run).

Table G demonstrates the polymerization of AZZ 902 at higher temperature (40 degrees C.) for different concentrations of Betaine. The results are also compared to solutions containing an additional amount of 5% glycine. These results show that 5% Betaine stabilize the AZZ 902 better than 5% glycine, confirming the hypothesis that Betaine is a better stabilizer than glycine. In addition, Table G shows that at a high temperature (40 degrees C.), the addition of 1% Betaine has little effect on the polymerization of zirconium, while at 8% Betaine the Zr species are completely stabilized. Moreover, similar to the observations obtained at room temperature, the Al species are less influenced by Betaine or glycine in the employed ranges of concentration. The sample with 1% Betaine remains a liquid for at least 630 days, and present gellation at 721 days. On the other hand, the samples with 5% and 8% Betaine are free flowing liquid solution up to 721 days.

For purposes of comparison AZZ 902 was used with three different additives, i.e. 3% Betaine vs. 3% glycine and 3% Betaine hydrochloride as described in Tables H and I. At such concentration, the Betaine hydrochloride induced precipitation of the antiperspirant active after 1 week, and therefore the experiment was terminated. On the other hand, the Betaine was superior to glycine for the stabilization of AZZ 902, yielding lower $f_{P1}$ values. In addition, both Betaine and glycine-containing samples are free flowing liquids after 721 days at room temperature (Table H). On the other hand, at 40 degrees C., the sample containing 5% Betaine remains a liquid, while that containing 5% glycine is a gel at 720 days (Table I).

TABLE G

SEC results for the 30% AZZ-902 solution with various concentrations of Betaine while aging at 40 degrees C.

| Time | 1% Betaine | | | 5% Betaine | | | 8% Betaine | | |
|---|---|---|---|---|---|---|---|---|---|
| (days) | Peak 1 | Peak 4 | Peak 5 | Peak 1 | Peak 4 | Peak 5 | Peak 1 | Peak 4 | Peak 5 |
| 21 | 0.410 | 0.164 | 0.138 | 0.203 | 0.151 | 0.130 | | | |
| 22 | | | | | | | 0.171 | 0.152 | 0.140 |
| 42 | 0.426 | 0.139 | 0.202 | 0.184 | 0.089 | 0.165 | 0.216 | 0.126 | 0.141 |
| 64 | | | | | | | 0.177 | 0.113 | 0.159 |
| 72 | 0.460 | 0.085 | 0.164 | 0.236 | 0.065 | 0.155 | | | |
| 78 | | | | | | | 0.219 | 0.096 | 0.158 |
| 105 | 0.460 | 0.073 | 0.160 | 0.261 | 0.061 | 0.156 | | | |
| 108 | | | | | | | 0.215 | 0.080 | 0.151 |
| 136 | | | | | | | 0.219 | 0.074 | 0.174 |
| 144 | 0.466 | 0.060 | 0.166 | 0.285 | 0.078 | 0.159 | | | |
| 630 | *liq | *liq | *liq | | | | | | |
| 721 | **gel | **gel | **gel | *liq | *liq | *liq | *liq | *liq | *liq |

*liq - sample observed as a free-flowing liquid (visual observation, no SEC data run).
**gel - sample observed as a gelled mass that does not flow (visual observation).

TABLE H

SEC results for the 30% AZZ-902 solution with various additives while aging at room temperature.

| Time | 3% Betaine | | | 3% glycine | | | 3% Betaine HCl | | |
|---|---|---|---|---|---|---|---|---|---|
| (days) | Peak 1 | Peak 4 | Peak 5 | Peak 1 | Peak 4 | Peak 5 | Peak 1 | Peak 4 | Peak 5 |
| 4 | 0.173 | 0.352 | 0.129 | 0.188 | 0.248 | 0.118 | 0.113 | 0.231 | 0.181 |
| 7 | 0.178 | 0.244 | 0.125 | 0.197 | 0.231 | 0.110 | 0.110 | 0.193 | 0.188 |
| 11 | 0.185 | 0.253 | 0.113 | 0.200 | 0.213 | 0.104 | pp | pp | pp |

TABLE H-continued

SEC results for the 30% AZZ-902 solution with various additives while aging at room temperature.

| Time | 3% Betaine | | | 3% glycine | | | 3% Betaine HCl | | |
|---|---|---|---|---|---|---|---|---|---|
| (days) | Peak 1 | Peak 4 | Peak 5 | Peak 1 | Peak 4 | Peak 5 | Peak 1 | Peak 4 | Peak 5 |
| 18 | 0.211 | 0.237 | 0.113 | 0.229 | 0.201 | 0.116 | | | |
| 25 | 0.193 | 0.223 | 0.126 | 0.211 | 0.175 | 0.113 | | | |
| 32 | 0.222 | 0.216 | 0.107 | 0.237 | 0.161 | 0.126 | | | |
| 46 | 0.216 | 0.202 | 0.110 | 0.247 | 0.159 | 0.120 | | | |
| 74 | 0.216 | 0.184 | 0.121 | 0.247 | 0.135 | 0.128 | | | |
| 109 | 0.227 | 0.165 | 0.134 | 0.241 | 0.117 | 0.130 | | | |
| 144 | 0.218 | 0.124 | 0.130 | 0.266 | 0.091 | 0.146 | | | |
| 721 | *liq | *liq | *liq | *liq | *liq | *liq | | | |

*liq - sample observed as a free-flowing liquid (visual observation, no SEC data run).
***pp - precipitate occurred in sample.

TABLE I

SEC results for the 30% AZZ-902 solution with various additives while aging at 40 degrees C.

| Time | 5% Betaine | | | 5% glycine | | | 5% Betaine HCl | | |
|---|---|---|---|---|---|---|---|---|---|
| (days) | Peak 1 | Peak 4 | Peak 5 | Peak 1 | Peak 4 | Peak 5 | Peak 1 | Peak 4 | Peak 5 |
| 3 | | | | | | | ***pp | ***pp | ***pp |
| 21 | 0.203 | 0.151 | 0.130 | 0.248 | 0.102 | 0.159 | | | |
| 42 | 0.184 | 0.089 | 0.165 | 0.253 | 0.091 | 0.172 | | | |
| 72 | 0.236 | 0.065 | 0.155 | 0.273 | 0.068 | 0.177 | | | |
| 105 | 0.261 | 0.061 | 0.156 | 0.294 | 0.037 | 0.183 | | | |
| 144 | 0.285 | 0.078 | 0.159 | 0.308 | 0.030 | 0.186 | | | |
| 360 | | | | *liq | *liq | *liq | | | |
| 721 | *liq | *liq | *liq | **gel | **gel | **gel | | | |

*liq - sample observed as a free-flowing liquid (visual observation, no SEC data run).
**gel - sample observed as a gelled mass that does not flow (visual observation).
***pp - precipitate occurred in sample.

Example 3

Summit Z522 with Betaine

As shown by the data in Table J, the use of Betaine with Summit Z522 antiperspirant active did not show a stabilizing effect, either at room temperature or at a higher temperature aging in solution. In both cases, the solutions containing Betaine gelled faster than solutions without Betaine. The Summit Z522 antiperspirant active was the only active that was received in a 29% solution, and approximately 4 weeks old. In four weeks the polymerization of the active reached high molecular weights and the addition of Betaine may have triggered the gelation by cross-linking the large polymer species.

TABLE J

Results for the 29% Summit Z522 solution with 8% Betaine while aging at room temperature or 40 degrees C.

| Time | 0% Betaine | | 8% Betaine | |
|---|---|---|---|---|
| (days) | RT | 40 deg C. | RT | 40 deg C. |
| 7 | *liq | *liq | *liq | *liq |
| 36 | *liq | *liq | *liq | **gel |

TABLE J-continued

Results for the 29% Summit Z522 solution with 8% Betaine while aging at room temperature or 40 degrees C.

| Time | 0% Betaine | | 8% Betaine | |
|---|---|---|---|---|
| (days) | RT | 40 deg C. | RT | 40 deg C. |
| 57 | *liq | *liq | **gel | |
| 96 | **gel | **gel | | |

*liq - sample observed as a free-flowing liquid (visual observation, no SEC data run).
**gel - sample observed as a gelled mass that does not flow (visual observation).

What is claimed is:

1. A stabilized aluminum/zirconium/glycine salt comprising a Betaine of Formula I:

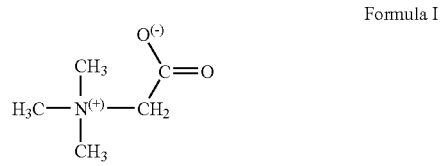

Formula I in a sufficient amount to have (a) an overall (Betaine+ glycine)/Zr ratio in the range of 0.1–3.0:1, (b) a ratio of Betaine to glycine of at least 0.001:1; and (c) sufficient Betaine so that at least 0.1% of the ratio of Betaine+ glycine is contributed by Betaine.

2. A stabilized salt according to claim 1 wherein the overall (Betaine+glycine)/Zr ratio is in the range of 0.7–1.5:1.

3. A stabilized salt according to claim 1 wherein the aluminum-zirconium glycine salt is a member of the group consisting of aluminum zirconium trichlorohydrex gly, aluminum zirconium pentachlorohydrex gly, aluminum zirconium tetrachlorohydrex gly, aluminum zirconium octachlorohydrex gly, aluminum zirconium trichlorohydrex gly propylene glycol complex, aluminum zirconium trichlorohydrex gly dipropylene glycol complex, aluminum zirconium tetrachlorohydrex gly propylene glycol complex, aluminum zirconium tetrachlorohydrex gly dipropylene glycol complex, and mixtures of any of the foregoing.

4. An antipersiprant product made with a stabilized salt of any one of claims 1, 2 or 3.

5. A deodorant product made with a stabilized salt of any one of claims 1, 2 or 3.

6. A stick antiperspirant and/or deodorant comprising:
    40–55% cyclomethicone; 20–30% stearyl alcohol; 7–15% talc; 15–22% of a salt according to claim 1 added in powder form; and 1–3% fragrance.

7. A roll-on antiperspirant and/or deodorant comprising:
    45–65% cyclomethicone; 0.1–10% cyclomethicone/dimethicone copolyol; 10–25% of a salt according to claim 1 in a solution as 25–45% actives on an anhydrous basis in water; 5–30% water; and 1–3% fragrance.

8. A soft solid antiperspirant and/or deodorant comprising: 40–70% elastomer in cyclomethicone; 5–15% polyethylene beads having a density in the range of 0.91–0.98 g/cm$^3$ and an average particle size in the range of 5–40 microns; 10–20% C12–15 alkylbenzoate; 0.1–25%% of a salt according to claim 1 added in powder form; 1–15% dimethicone; and 1–3% fragrance.

9. A gel antiperspirant and/or deodorant comprising:
    5–50% cyclomethicone; 0.1–10% cyclomethicone/dimethicone copolyol; 0–10% hydrogenated polyisobutene 250; 0–10% C12–15 alkylbenzoate; 0–10% dimethicone; 0.1–25% of a salt according to claim 1 added in powder form or as 10–25% of active in solution (25–45% actives on an anhydrous basis); 5–50%; and 1–3% fragrance.

* * * * *